United States Patent [19]
Clarke et al.

[11] Patent Number: 5,907,401
[45] Date of Patent: May 25, 1999

[54] DEVICE AND METHOD FOR PERFORMING AN OPTICAL HALL TEST

[75] Inventors: Frederick W. Clarke, Madison County; Joseph K. McDonald; Charles R. Christensen, both of Limestone County; John A. Grisham, Lauderdale County, all of Ala.

[73] Assignee: The United States of America as represented by the Secretary of the Army, Washington, D.C.

[21] Appl. No.: 08/937,250

[22] Filed: Sep. 3, 1997

[51] Int. Cl.⁶ .................................................. G01B 9/02
[52] U.S. Cl. ............................................. 356/346; 356/345
[58] Field of Search .................................. 356/345, 346

[56] References Cited

U.S. PATENT DOCUMENTS

| | | |
|---|---|---|
| 4,637,726 | 1/1987 | Walker et al. . |
| 4,818,881 | 4/1989 | Tanton et al. . |
| 5,210,417 | 5/1993 | Grisham et al. . |
| 5,539,518 | 7/1996 | Bennett .................................... 356/346 |

*Primary Examiner*—Robert H. Kim
*Attorney, Agent, or Firm*—Hugh P. Nicholson; Freddie M. Bush; Hay Kyung Chang

[57] ABSTRACT

The device and method for performing an optical Hall test provide means for non-destructive measurement of free carrier concentration or effective mass in semiconductor materials using Faraday rotation spectra. A beam emitted by a Fourier transform infrared (FTIR) spectrometer is transmitted through the sample that is mounted between a polarizer and analyzer and the opposite poles of a magnet before finally being incident on a detector. The ratio of the samples's transmission spectrum with the magnetic field on to that with the magnetic field off is converted, through a suitable mathematical formula, to Faraday rotation. The rotation is, then, plotted versus the square of the wavelength. The slope of the graph at longer wavelengths is directly proportional to the carrier concentration and the effective mass. With one known, the other can be easily determined.

2 Claims, 2 Drawing Sheets

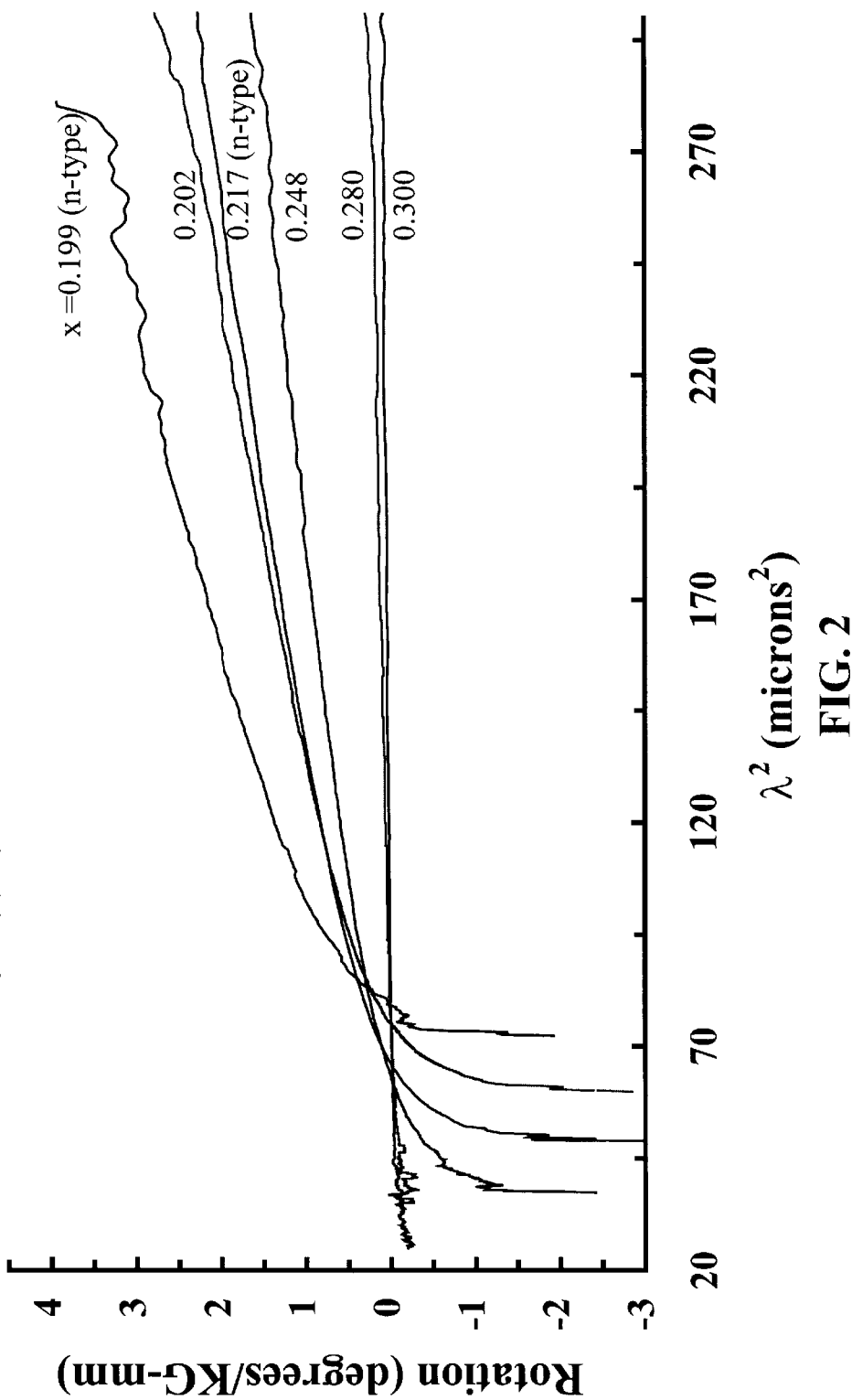

DEVICE AND METHOD FOR PERFORMING AN OPTICAL HALL TEST

The invention described herein may be manufactured, used and licensed by or for the Government for governmental purposes without the payment to us of any royalties thereon.

BACKGROUND OF THE INVENTION

The Hall test, invented in 1879 by E. H. Hall and improved by L. J. van der Pauw in 1958, is commonly used to measure carrier concentration and mobility in semiconductor samples. It requires four electronic contacts to be soldered to the surface of the semiconductor sample. The test is time-consuming (on the order of a few hours) and is also subject to large errors due to contamination introduced by soldering. In low-mobility samples such as n-type silicon, the contamination typically results in a 10% or more rise in carrier concentration and approximately 10% drop in mobility due to infusion of the solder's impurities into the sample. In high mobility materials such as mercury cadmium telluride (HgCdTe) and indium antimonide (InSb), soldered contacts can easily result in excess of 100% error in carrier concentration and 50% or more error in mobility. This is due to the "doping" effect of the solder's impurities into the sample at soldering temperatures. For this reason, particularly in thin films, the Hall test is destructive, usually requiring an expendable or "witness" sample that cannot be subsequently used for device manufacture.

Faraday rotation is the rotation of the plane of polarization of light as it passes through a sample in the presence of a magnetic field whose field lines are in the direction of the light. In semiconductors, Faraday rotation has two components: the plasma component which is due to free carriers and the interband component which is due to free carrier transitions across the band gap. The plasma component ($\theta_n$) is proportional to the free carrier concentration (N), the effective mass ($m^*$) and the wavelength of light ($\lambda$) used according to $$\theta_n = \frac{qBL}{8\pi^2 c^3 \varepsilon_0 m^2 n} \left( \frac{N\lambda^2}{m^{*2}} \right) \quad (1)$$

where q is the electron charge, c is the speed of light, $\varepsilon_0$ is the permittivity of free space, m is the electron mass (these values are constants along with $\pi$), B is the magnetic field strength used, L is the thickness of the sample, and n is the refractive index of the material. By far the most popular known method of determining free carrier effective mass in semiconductors is via measurement of Faraday rotation at a single wavelength as the light travels through the semiconductors. Faraday rotation utilizing a single wavelength is useful in measuring the plasma component of the rotation in semiconductors such as silicon (Si) and gallium arsenide (GaAs) where the interband component is negligible due to their relatively wide band gaps. But in narrow band gap semiconductors such as HgCdTe and InSb where the interband component is significant, the plasma component of the Faraday rotation cannot be isolated from the interfering interband component. Indeed, until the invention of this device, measurement of electron effective mass in narrow band gap semiconductors such as HgCdTe and InSb was very limited if not impossible. HgCdTe was discovered as a promising infrared detector material in 1959. The electron effective mass is an important parameter in the design of detectors but it could not be measured in HgCdTe and other narrow band gap semiconductors such as low-doped InSb. Several calculated values of effective mass of HgCdTe were reported in the early 1980's but these were seen to be significantly inaccurate, especially at higher temperatures. Room temperature values were of particular interest but were unavailable. Effective masses of free electrons in HgCdTe and InSb were recently measured for the first time using this device.

SUMMARY OF THE INVENTION

The device and method for performing an optical Hall test measures free carrier concentration in semiconductors by optical means, provided certain constants of the material are known. It can be used as a nondestructive replacement for the carrier concentration measurement portion of the Hall test which is currently the industry standard for measuring carrier concentration and mobility. The infrared Faraday rotation spectrum of a sample is measured and plotted as a function of the square of the wavelength. The slope of the flat portion of the plot is equal to a constant times the carrier concentration. The constant can be determined provided two required constants of the material, namely, the refractive index and the carrier's effective mass, are known. Alternatively, if the refractive index and carrier concentration are known, the carrier's effective mass can be determined. Effective mass is not available from a Hall test.

Carrier mobility can also be determined optically from the ratio of the carrier's Faraday rotation to its infrared absorption. This method requires the absorption due only to the carrier itself. In many semiconductors this is obtained directly from the infrared absorption spectrum. In semiconductors with significant populations of both free electrons and holes, a method is required for separating their absorption components.

DESCRIPTION OF THE DRAWING

FIG. 2 graphically illustrates the relationship between the Faraday rotation and $\lambda^2$ in six HgCdTe samples, four nearly intrinsic and two n-type samples with cadmium mole fraction, x, between 0.20 and 0.30.

DESCRIPTION OF THE PREFERRED EMBODIMENT

Figure 1:
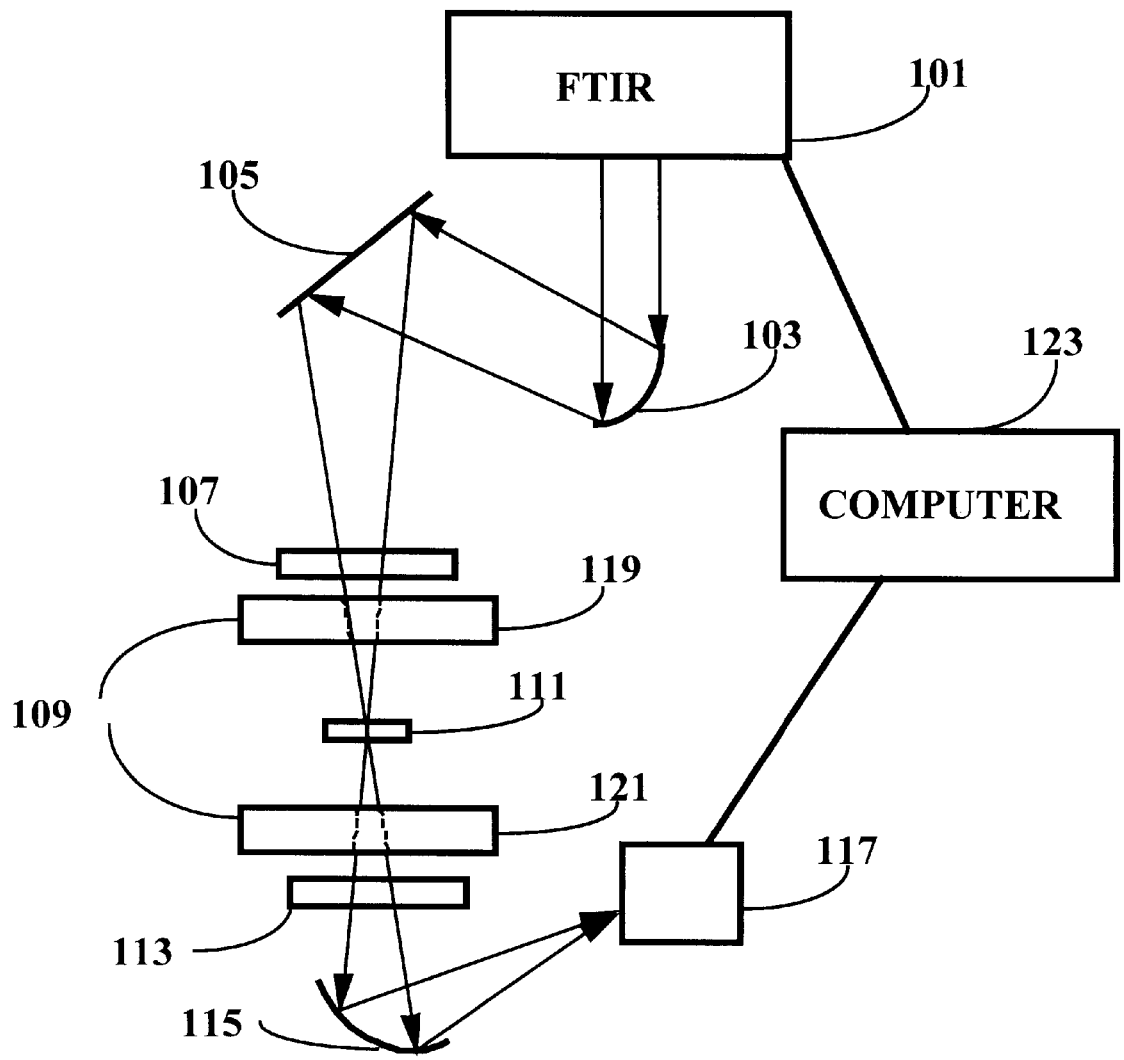
FIG. 1 show the diagram of a preferred embodiment of the device that can determine carrier concentration or effective mass according to the invention.

Referring now to the drawing wherein like numbers represent like parts in each of the figures and the lines with arrowheads represent optical paths, the operation of the device for performing an optical Hall test and the significance of the plots produced by the operation are explained.

The device used to generate the graphs is depicted in FIG. 1. As shown in the figure, commercially available Fourier transform infrared spectrometer (FTIR) 101 having a spectral range of 5 to 20 microns emits a beam of random polarization (other spectral ranges, however, may be used). The light is focussed and redirected by first focussing mirror 103 to second mirror 105 which again redirects the beam to polarizer 107. The plane-polarized beam from the polarizer then passes through a hole drilled in first pole 119 of split electro-magnet 109. The beam subsequently proceeds through semiconductor sample 111, through a hole drilled in second pole 121 of the magnet and onto analyzer 113. The analyzer is another polarizer which is set at a bias angle $\theta_B$ relative to polarizer 107. With the magnetic field turned on, the quantity of light passing through the analyzer is proportional to the amount of rotation of the plane of polarization the light undergoes as it passes through the sample. The light psssing through analyzer 113 is then focussed at third mirror 115 and redirected to detector 117. The detector produces an electronic signal that is proportional to the quantity of light detected and transmits the signal to computer 123 which may be physically separate from but coupled to FTIR 101 or be internal to the FTIR. Using the signal resulting from light passing through the sample with the magnetic field off as a reference, the computer produces transmission signal, T, which is the ratio of the signal resulting from the light passing through the sample with magnetic field on to the signal resulting from the light passing through the sample with the magnetic field off at any given wavelength. The computer or the FTIR, if the FTIR incorporates the computer, performs these measurements automatically at approximately 400 points across the 5 to 20 micron band. All the values of T are then converted, point by point, to Faraday rotation by computer 123 using the known formula, $$\Theta_R = \frac{(\text{Arccos}[SQRT(T)\cos(\theta_b)] - \theta_b)}{B} \quad (2)$$

where $\Theta_R$ is the total rotation due to sample 111 at one of the approximately 400 wavelengths. The converted points are plotted as total rotation vs. the square of the wavelength. FIG. 2 shows the Faraday rotation v. $\lambda^2$ for six HgCdTe samples, four nearly intrinsic and two n-type samples with mole fraction (x) of cadmium ranging between 0.20 and 0.30. These six spectra were obtained at room temperature (296 K.°). As can be seen in the figure, the curved parts of these spectra at the extreme left show negative rotation due to the interband component which becomes very steep at the band gap wavelength. However, the plasma component dominates the spectra at longer wavelengths on the right side where the plot becomes practically linear with a slope that is proportional to the sample's carrier concentration and effective mass according to equation (1) set out, supra, cited again for ease of reference:

$$\theta_n = \frac{qBL}{8\pi^2 c^3 \varepsilon_0 m^2 n} \left(\frac{N\lambda^2}{m^{*2}}\right) \quad (1)$$

In the linear region of the spectra, the slope of the plot is represented by all the terms on the right side of the equal sign in equation (1) except for $\lambda^2$. With the refractive index and carrier effective mass of the sample material known, the only unknown quantity in equation (1) is the carrier concentration, N. Alternatively, if the refractive index and the carrier concentration are known, the effective mass, $m^*$, can be determined. This simple technique solves the problem of separating rotation components, thereby eliminating the need for complicated and unreliable mathematical and empirical band gap models. The plasma component (equation 1) appears as the slope of the plot and the interband component appears as the intercept of the linear portion extended to the rotation axis. The accuracy is limited by the strength of the detector-produced electronic signal, which, in turn, is determined by the strength of the magnetic field, the light source intensity, distortion due to the polarizer and the analyzer, spectrum noise and the resolution of the plot. The slopes can be determined with the present device with an accuracy of +/−5% which results in a +/−5% determination of carrier concentration or, alternatively, an effective mass determination of +/−2 to 3%. This is a better accuracy than is generally attainable with the Hall test. Further, this device is much faster, capable of measurements in extremely small areas of the sample and, most importantly, it is nondestructive and suitable for on-line screening of semiconductor materials on the production line.

The carrier mobility, $\mu$, can be determined using a ratio of the free carrier's Faraday rotation (plasma component) and its absorption at a particular infrared wavelength in the plasma region according to $$\mu = \frac{C}{KLB}\theta_n \quad (3)$$

where K is the intraband absorption due to the free carrier itself and C is the mobility constant which is assumed to be known for the sample material at the desired temperature and at the same wavelength as the Faraday rotation. In semiconductors with low intrinsic or natural carriers, such as Si, Ge or GaAs, the absorption due to the carrier, K, is obtained directly from the free carrier absorption region (at the same wavelength at which C and $\theta_n$ were determined) of the absorption spectrum. The mobility is then calculated from equation (3). This method requires the absorption due only to the carrier itself. In materials with high intrinsic carrier concentration, such as low-doped InSb and HgCdTe, both holes and electrons are present in significant numbers. For these materials, a method for separating their absorption components is required.

Although a particular embodiment and form of this invention has been illustrated, it is apparent that various modifications and embodiments of the invention may be made by those skilled in the art without departing from the scope and spirit of the foregoing disclosure. Accordingly, the scope of the invention should be limited only by the claims appended hereto.

We claim:

1. A non-intrusive method for measuring free carrier concentration and effective mass of a semiconductor sample, said method comprising the steps of:

A) providing a hole in each of the two opposite poles of a split electromagnet so as to allow the passage of light through the holes;

B) mounting a semiconductor sample between the two opposite poles of the split electromagnet;

C) activating the magnet to create a magnetic field;

C-i) transmitting a pre-determined wavelength band of light through an FTIR;

C-ii) directing the pre-determined wavelength band of light through a polarizer to plane-polarize the light;

D) re-directing the plane-polarized light through the poles of the magnet and through the semiconductor sample;

E) further transmitting the plane-polarized light through an analyzer having a pre-set polarization orientation;

F) detecting the amount of light emanating from the analyzer;

F-i) sending detector signal to a computer;

F-ii) Fourier-transforming the detector signal to calculate intensities at pre-determined wavelengths;

G) inactivating the magnet and performing the steps A), B), C-i), C-ii), D), E), F), F-i) and F-ii) in the order listed;

G-i) calculating the ratio of the light intensity with and without the magnetic field at each pre-determined wavelength of the band;

H) measuring the Faraday rotation undergone by the light when passing through the sample at each pre-selected wavelength of the band;

J) plotting a graph of the Faraday rotation as a function of $\lambda^2$, yielding a slope of the graph at longer wavelengths; and K) determining from the slope, using appropriate mathematical formulas, the separate plasma and interband components of the Faraday rotation, said determination yielding the free carrier concentration or effective mass of the semiconductor sample.

2. A non-intrusive method for measuring free carrier concentration and effective mass of a semiconductor sample, said method comprising the steps of:

A) providing a split electromagnet having an aperture in each of the two opposite poles thereof;

B) mounting a semiconductor sample between the two opposite poles of the split electromagnet;

C) activating the magnet to create a magnetic field;

D) transmitting simultaneously plane-polarized light of various wavelengths through the poles of the magnet and through the semiconductor sample;

E) further transmitting the light through an analyzer having a pre-set polarization orientation;

F) detecting the amount of light emanating from the analyzer;

G) inactivating the magnet and performing the steps A), B), D), E) and F) in the order listed;

H) calculating at discrete wavelengths the Faraday rotation undergone by the light when passing through the sample;

I) plotting a graph of the Faraday rotation as a function of $\lambda^2$, yielding a slope of the graph at longer wavelengths; and J) determining from the slope, using appropriate formulas, the separate plasma and interband components of the Faraday rotation, said determination yielding the free carrier concentration or effective mass of the semiconductor sample, depending on pre-selected known constants.

* * * * *